United States Patent [19]

DeVaughn

[11] Patent Number: 5,330,899
[45] Date of Patent: Jul. 19, 1994

[54] CALIBRATED INOCULATION ASSEMBLY AND METHOD OF PRESERVING STERILITY

[75] Inventor: Donald H. DeVaughn, San Francisco, Calif.

[73] Assignee: Bio-Plas, Inc., San Francisco, Calif.

[21] Appl. No.: 959,617

[22] Filed: Oct. 13, 1992

[51] Int. Cl.$^5$ ............................................. C12Q 1/24
[52] U.S. Cl. ...................................... 435/30; 206/363;
206/366; 206/439; 206/443; 220/265; 220/268;
435/292; 435/293; 435/294; 604/1; 604/3;
604/415
[58] Field of Search ................. 435/30, 292, 293, 294;
206/363, 366, 439, 443, 364, 438; 215/250,
DIG. 3; 220/265, 268; 604/1, 3, 415

[56] References Cited

U.S. PATENT DOCUMENTS

| | | | |
|---|---|---|---|
| 3,147,197 | 9/1964 | Connors | 435/30 X |
| 3,772,154 | 11/1973 | Isenberg et al. | 435/292 X |
| 3,874,503 | 4/1975 | Shaffer et al. | 435/294 X |
| 3,915,806 | 10/1975 | Horlach | 435/30 |
| 4,010,077 | 3/1977 | Pardos | 435/294 |
| 4,657,869 | 4/1987 | Richards et al. | 435/287 |
| 4,687,746 | 8/1987 | Rosenberg et al. | 435/292 |
| 4,690,676 | 9/1987 | Moulding, Jr. et al. | 604/189 |
| 4,927,019 | 5/1990 | Haber et al. | 206/365 |
| 5,048,684 | 9/1991 | Scott | 206/364 |

Primary Examiner—Robert J. Warden
Assistant Examiner—Krisanne M. Thornton
Attorney, Agent, or Firm—Flehr, Hohbach, Test, Albritton & Herbert

[57] ABSTRACT

A sterile inoculation assembly includes an inoculation device (20), a storage container (84) and a handling tool (60). The inoculation device (20) includes an elongated body (22) having an inoculation end (26) and an opposed gripping end (24). The container (84) is formed with at least one cavity (86) with an opening (88) thereto. The cavity (86) is dimensioned to receive the inoculation device (20) in an orientation which permits the gripping end (24) to be grasped through the opening (88). A sheet-like cover (98) is positioned across the opening (88) to seal it and to retain the inoculation device (20) in the cavity (86). The cover (98) is capable of being punctured for grasping of the gripping end (24) and removal of the inoculation device (20) by a handling tool (60). This handling tool (60) telescopically engages the gripping end (24) for releasible securement thereto. Removal of the inoculation device (20) by the handling mechanism (60) is permitted while preserving the sterile integrity of the inoculation device (20). A method for removing the sterile inoculation device (20) from the sterile storage container (84) while maintaining the inoculation end (26) of the inoculation device (20) in a sterile condition also is provided.

43 Claims, 6 Drawing Sheets

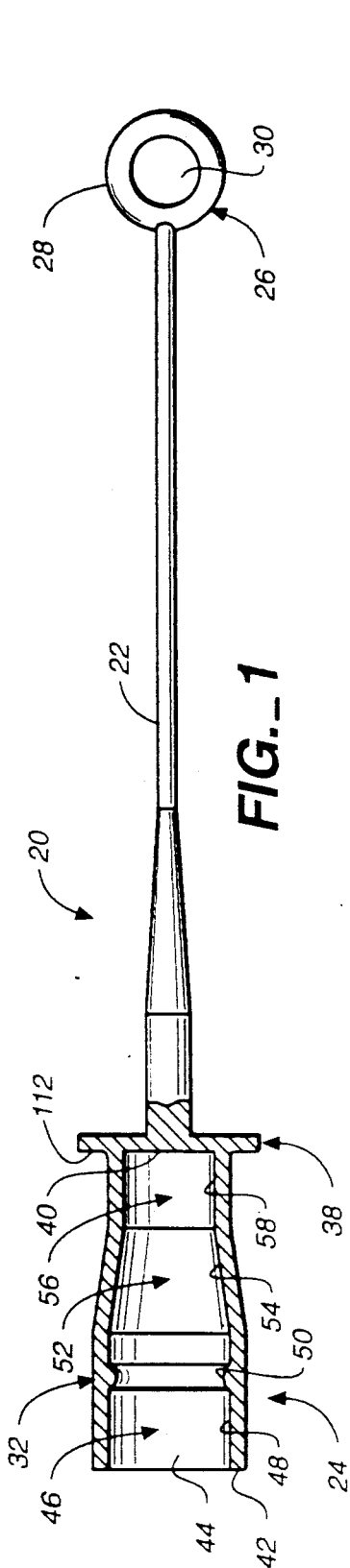
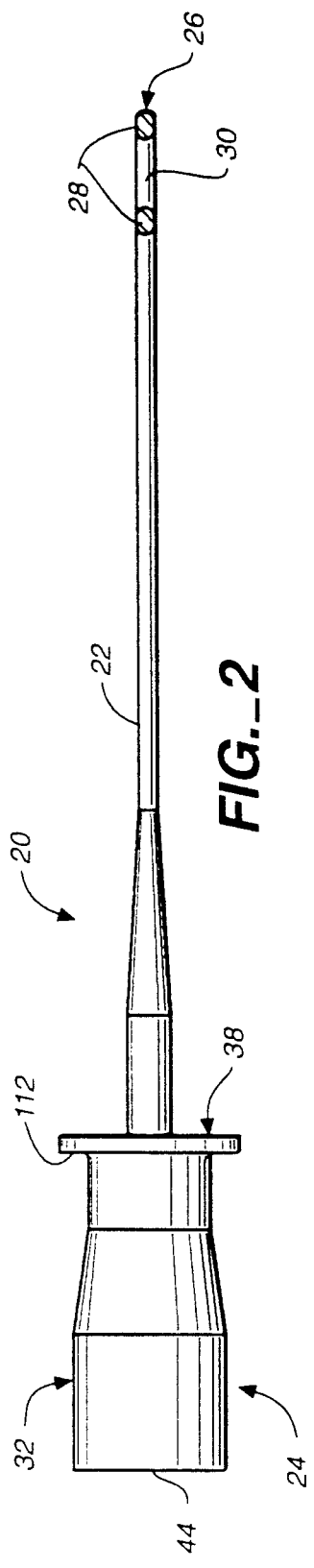
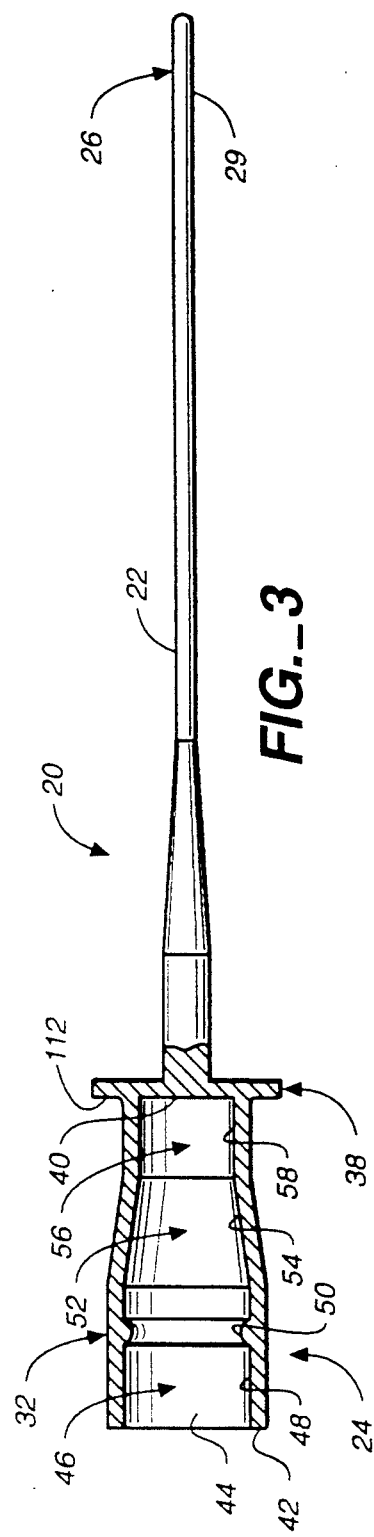

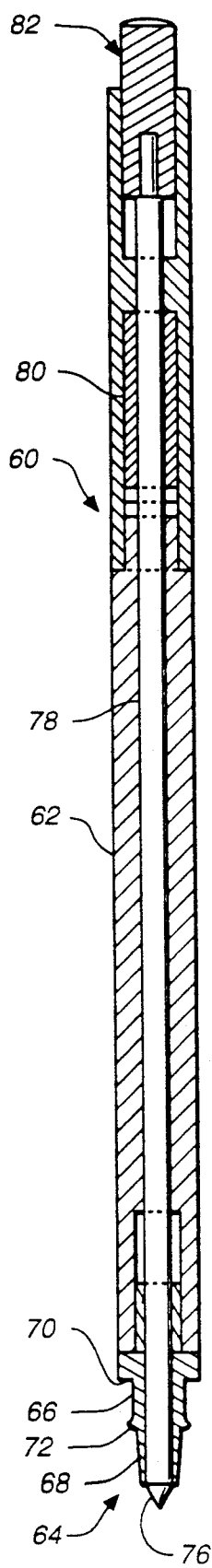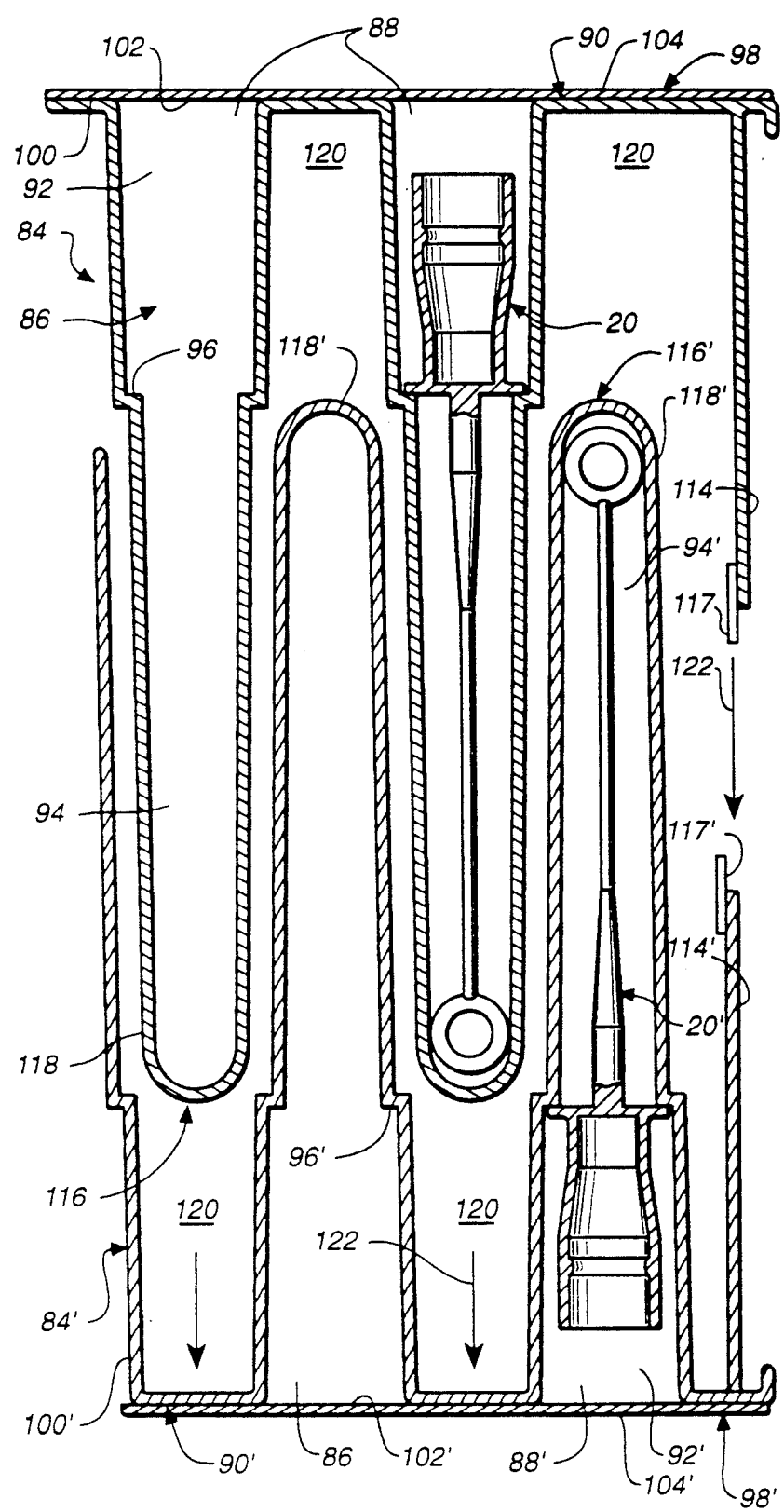
FIG._4    FIG._9

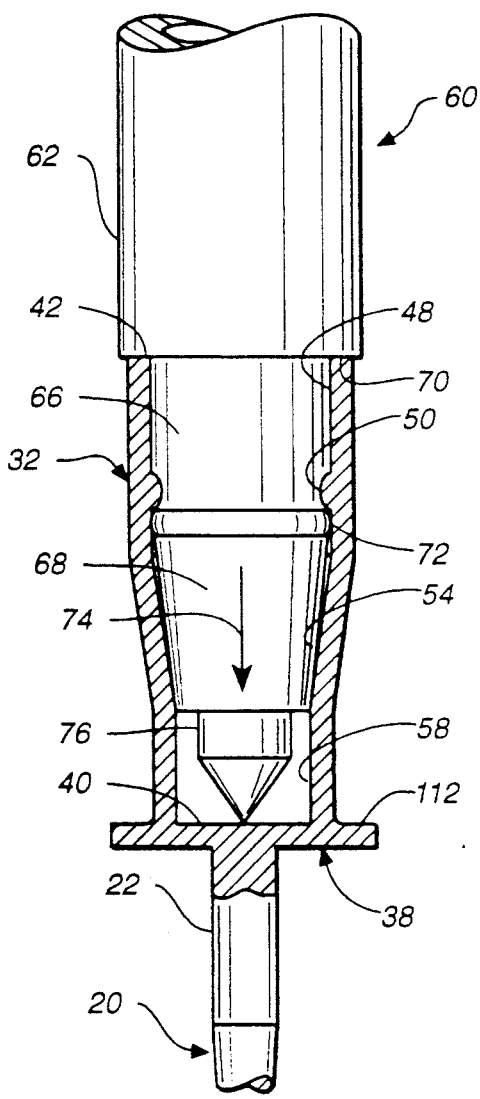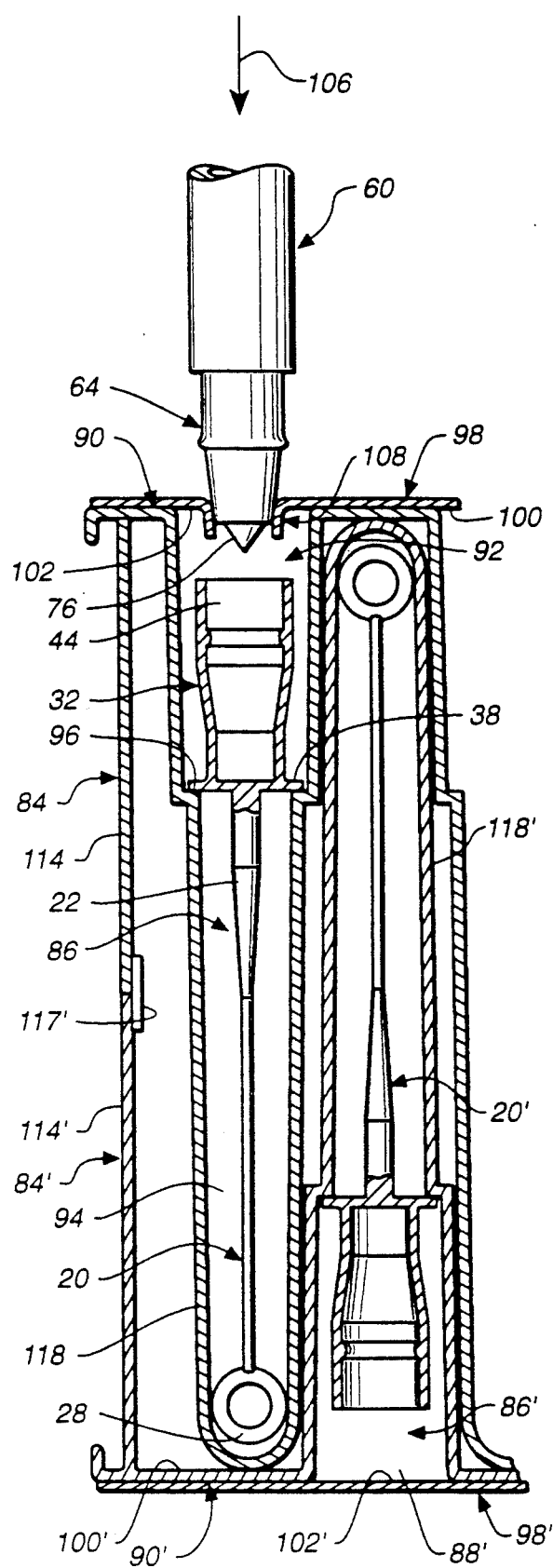
FIG._5                FIG._6A

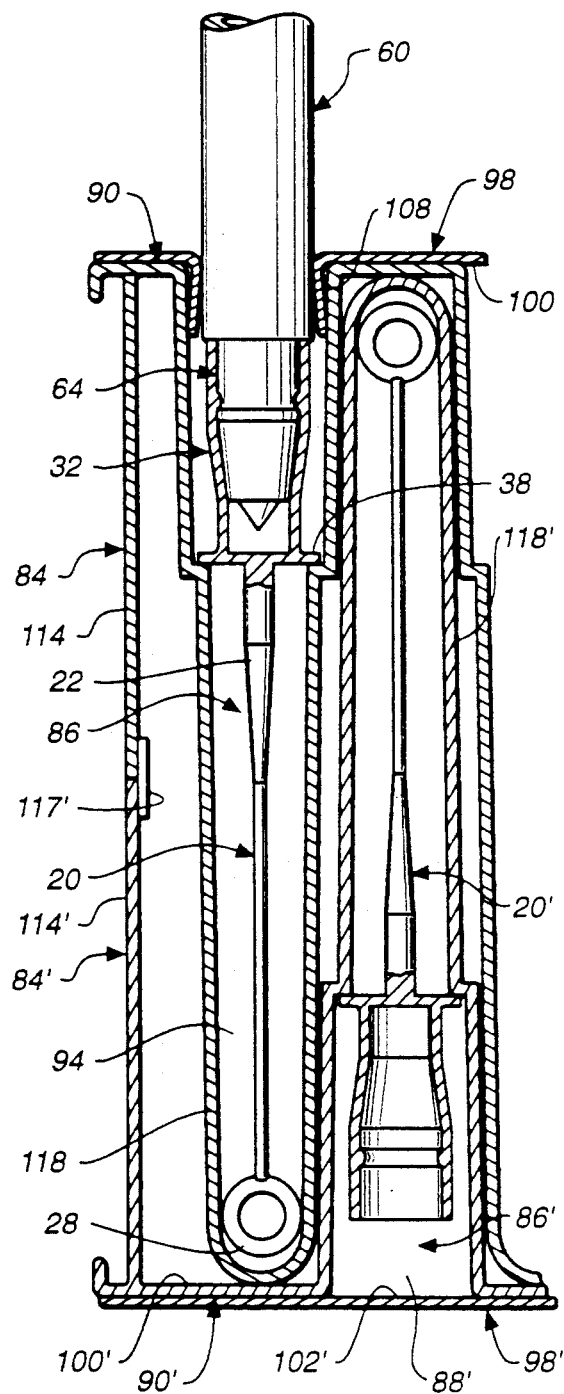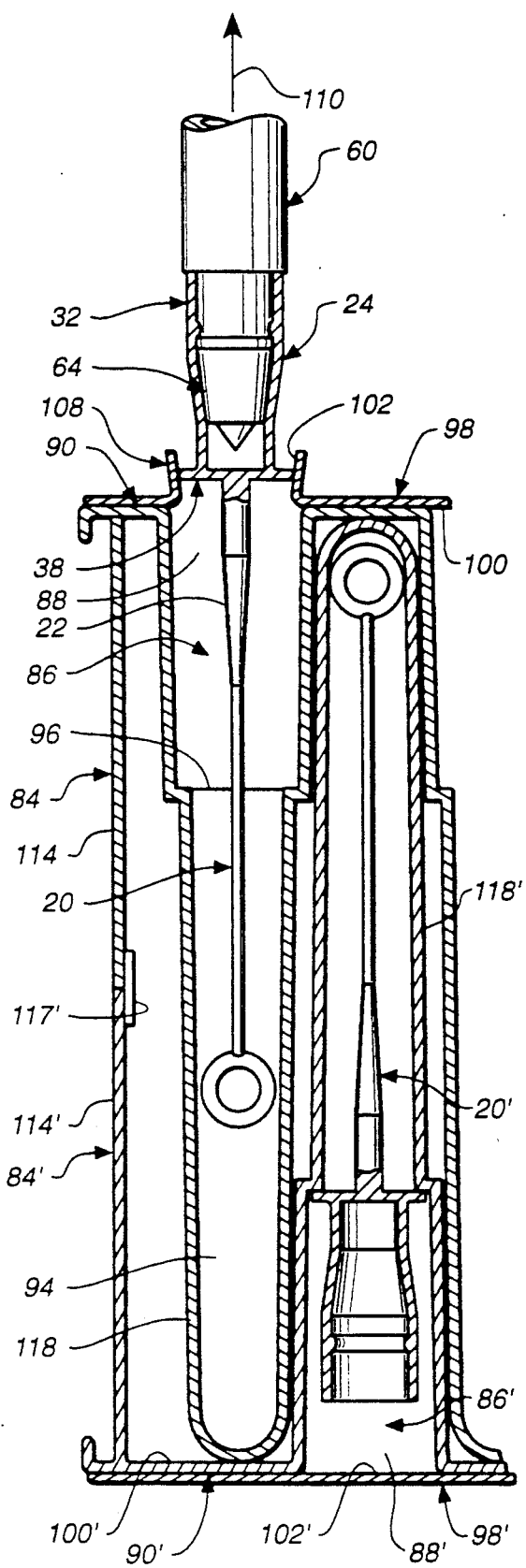
FIG._6B  FIG._6C

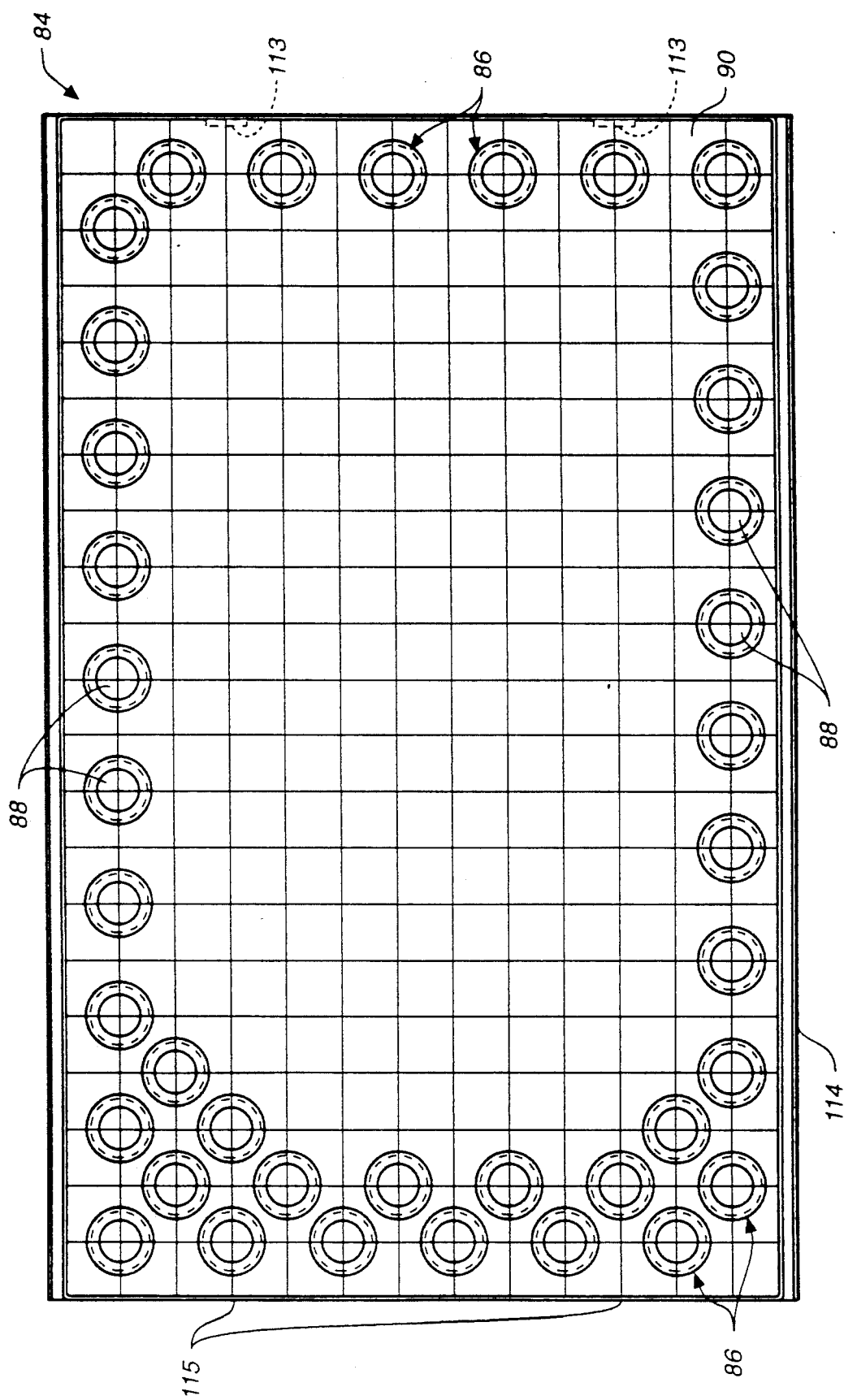
FIG._7

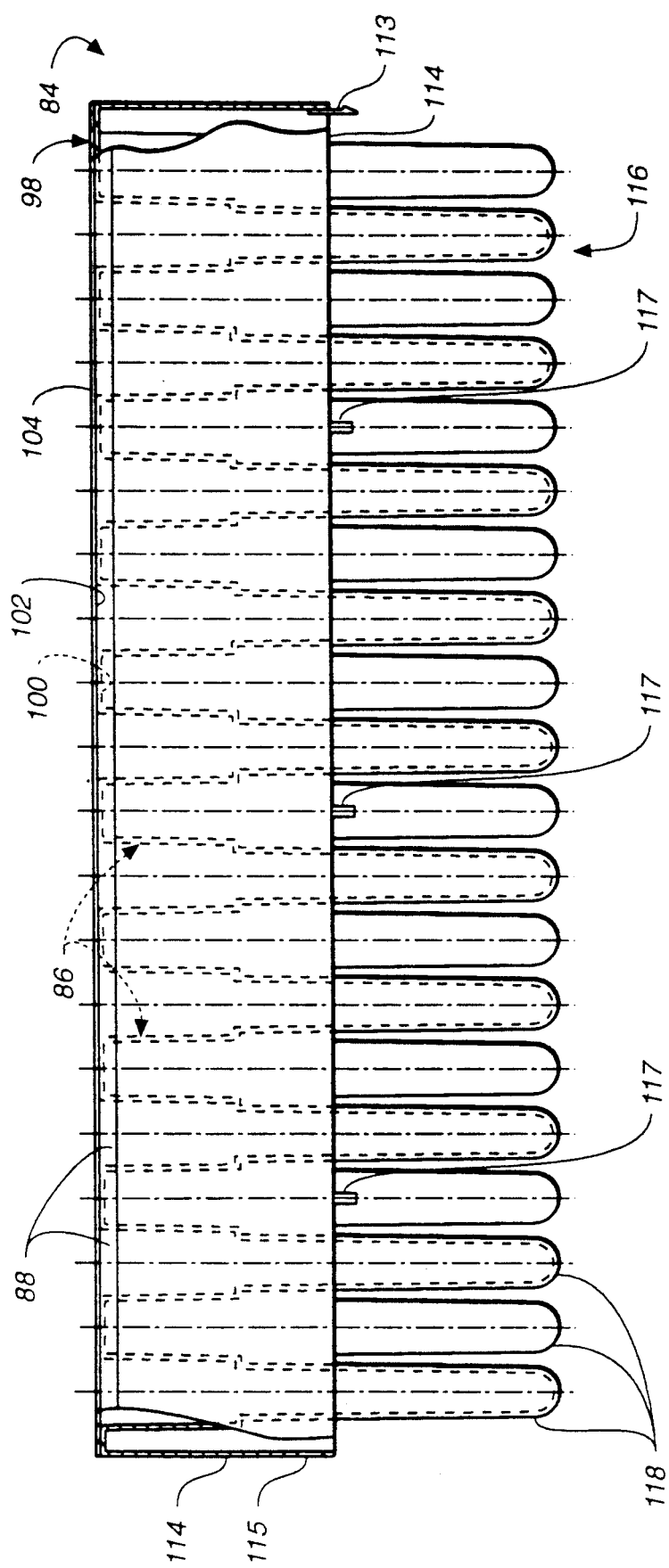
FIG._8

CALIBRATED INOCULATION ASSEMBLY AND METHOD OF PRESERVING STERILITY

BACKGROUND OF THE INVENTION

1. Field of the Invention

The present invention relates, generally, to inoculation devices and, more particularly, to apparatus and methods used to store and preserve the sterility of inoculation devices.

2. Description of the Related Art

As the biotechnology, pharmaceutical and related industries experience unprecedented growth, their laboratory research and development proportionately expands. Thus, research precision has become increasingly important, often distinguishing their efforts. Through research evolution, research apparatus and techniques, once thought to represent the industry standard, are continually being replaced by better, more efficient and accurate apparatus and techniques.

Inoculation devices or tools are generally not considered precision research instruments. Manufacturers have not found it profitable, for example, to expend research funds to improve the precision of inoculation devices. Accordingly, significant strides to increase quantitative precision and sterile packaging of inoculation devices is greatly lacking.

Traditional laboratory inoculation techniques have remained rather crude, quantitatively inaccurate and potentially unsterile. Typically, after a desired microorganism has been successfully incubated in a nutrient broth substance, it is necessary to further colonized the micro-organism so that the particular strain can be identified, researched or experimented on. This procedure requires extracting a predetermined quantity of the inoculant from the broth and implanting or inoculating a nutrient medium, or blood agar, so that the microorganism can be grown under more controlled conditions. Using an inoculation device having an inoculating end, which is usually either needle-shaped or includes a loop end, an approximate quantity of the cultured broth is withdrawn therefrom by immersing the inoculating end in the broth. Subsequently, the inoculant is spread and implanted in the nutrient rich medium (agar) by contacting the inoculating end with the nutrient agar. Growth is stimulated by incubating the agar, for example, at approximately 37° C. which simulates body conditions. This incubation period, depending on the rate of growth of the micro-organism which in some cases doubles every 20 minutes, is typically 24 hours. Subsequently, the colonized microorganism may be identified, studied or be the subject of experimentation.

Inoculation tools, in general, have not changed radically since the introduction of the inoculation loop. Earlier inoculation ends where comprised of metallic wires or needles. Often platinum or silver were used because of their higher conductive resistance. Metallic inoculation devices usually require sterilization before each use so that the inoculant is not contaminated by the growth or existence of other contaminating organisms or bacteria attached to the inoculating ends. By placing the inoculating end in an open flame, such as a bunsen burner, until the loop becomes red hot, the loop can be sterilized. The research technician must then wait for the loop to air cool so that contact with the inoculant will not kill the microorganisms therein.

Despite its crude application, metallic inoculating ends are still in use today. One problem associated with these devices is that this technique is generally time consuming. Often, several different types of microorganism colonies are being cultured consecutively. Valuable time is expended because the inoculating end must be sterilized after contact with each different inoculant or nutrient agar. Thus, the technician must complete the entire sterilization cycle after each use. Furthermore, since the metallic ends are held over an open flame, the length of the inoculating device must be fairly long to prevent conductive burning. Moreover, insulated handles are often required as a precaution and for ease of handling. Storage, however, becomes problematic when the devices are too long. Finally, materials such as platinum and silver, which are used because of their high conductive resistance, are much too costly. This cost factor is particularly important if one tries to overcome the time delay problems by using multiple metallic inoculation loops.

More recently, plastic inoculating devices have begun to replace metallic inoculating devices. While such plastic inoculation devices have decreased manufacturing costs, sterilization has become a problem. Heat sterilization over an open flame, of course, is inappropriate because the inoculating ends would either melt or substantially deform. Therefore, the inoculation devices must be sterilized by irradiation with radio-isotopes or an electron beam, or by auto-claving before packaging. Typically, a multitude of inoculating loops and needles are sterilized and then packaged in the same container. This method present many problems. Once the package is opened, the remaining inoculation devices become contaminated with time or if they are touched. Either the package must be used completely or you run the risk of inoculating future mediums with contaminated inoculants. Moreover, if the technician is not careful upon removal, the inoculating ends may become contaminated. Contact of the inoculating end against the sides of the bag is often sufficient to affect the sterility of the inoculating end.

This sterilization problem may be partially overcome by individually packaging the plastic inoculation devices and then sterilizing them. While this technique has been satisfactory for most uses, again, however, the loops often become contaminated upon removal from the bag. Moreover, removal from each individual package becomes tedious and time consuming, requiring repeated openings of individual containers. Storage also becomes problematic when these devices are amassed in bulk.

Another problem associated with plastic inoculation devices is that they tend to be extremely inaccurate. Tests have shown that the dispensing volumes of these current plastic inoculation devices may vary by as much as 60%. Part of this problem may be attributed to the techniques employed to calibrate the dispensing volume of the inoculation loop. Typically, the calibration of a dispensing volume of an inoculation loop is performed using the "Evan's Blue Dye" method. This method of calibration, although widely accepted, itself appears highly inaccurate. Thus, it is difficult to control the dispensing volume accuracy of the inoculation loop when the method employed to calibrate the dispensing volume is itself imprecise. As quantitative accuracy and research precision become increasingly desirable, this method of calibration is becoming obsolete and unacceptable. Thus, precision inoculations can be greatly compromised by these instruments.

SUMMARY OF THE INVENTION

Accordingly, the present invention facilitates controlled handling and management of the inoculation device, while further, maintaining the device out of contact with unsterile portions of the container mechanism.

Accordingly, it is an object of the present invention to provide an inoculation assembly and method of manufacture which more accurately dispenses a predetermined quantity of inoculant.

It is another object of the present invention to provide an inoculation assembly and method which maintains sterility of an inoculation device during storage in the container.

Still another object of the present invention is to provide an inoculation assembly and method which permits contamination free removal from the storage container.

It is a further object of the present invention to provide an inoculation device which is durable, compact, easy to maintain, has a minimum number of components, is easy to use by unskilled personnel, and is economical to manufacture.

The present invention includes a sterile inoculation assembly comprising, briefly, an inoculation device in the form of an elongated member having an inoculation end and an opposed gripping end. A container is further provided which includes a cavity and which defines an opening into the cavity. The cavity is dimensioned to receive the inoculation device in an orientation which permits the gripping end to be grasped through the opening. A sheet-like cover is positioned across the opening to seal it and to retain the inoculation device in the cavity. Further, the cavity, the inoculation device and an inner surface of said cover are sterile. The cover is formed of a material, such as a metallic foil, capable of being punctured for grasping of the gripping end and removal of the inoculation device through the opening while maintaining the inoculation device out of contact with unsterile portions of the container.

In another aspect of the present invention, an inoculation assembly is provided which includes the above-mentioned inoculation device. Furthermore, a handling tool is provided which is capable of telescopic engagement with the gripping end for releasible securement thereto. A retaining structure provided on at least one of the gripping end and the handling tool releasably couples the tool and inoculation devices in telescopic engagement.

In yet another aspect of the present invention, an inoculation storage kit is provided which includes a plurality of the above-mentioned inoculation devices stored in a container which is adapted to individually store each device in a sterile environment. Further, the above-mentioned handling tool is included which permits removal from the container while maintaining the inoculation device out of contact with unsterile portions of the container.

A method for removing a sterile inoculation device from a sterile storage container while maintaining an inoculation end of the inoculation device in a sterile condition is also provided. The method comprises the steps of puncturing a wall, preferably the top wall, of the storage container proximate a gripping end of the inoculation device with a handling tool to form an access opening to the container. The inoculation device is coupled to the handling tool through the access opening by urging the handling tool toward the inoculation device until the inoculation device is releasably coupled to the handling tool. The inoculation device and the handling tool are then withdrawn out of the container through the access opening with the unsterile exterior surface of the punctured wall displaced away from the inoculation end as it is being removed from the container. Thus, the inoculation end of the device does not contact unsterile portions of the container during removal.

In still another aspect of the present invention, a method for calibrating an inoculation device casting mold is provided which increases the accuracy of the liquid carrying volume of the inoculation end, usually a loop. The calibration method comprises the steps of forming an inoculation device using the casting mold, immersing the inoculation device end in a first fluid having a known concentration of a radioisotope to retain a liquid volume of the first fluid on the inoculation end. The next step requires dispensing of the volume of first fluid into a second fluid usually by immersing the inoculation end in the second fluid. The second fluid has a known concentration of the radioisotope, for example, none. Subsequently, the radioisotope in the second fluid is measured, and using the known concentration of the radioisotope in the first fluid, the volume carried by the inoculation end can be determined. Additionally, the method can include adjusting the casting mold after determination of the volume carried by the inoculation end.

BRIEF DESCRIPTION OF THE DRAWINGS

The assembly of the present invention has other objects and features of advantage which will be more readily apparent from the following description of the Best Mode of Carrying Out the Invention and the appended claims, when taken in conjunction with the accompanying drawing, in which:

FIG. 1 is an enlarged top plan view, in partial cross-section, of the inoculation device constructed in accordance with the present invention and incorporating an inoculation loop end.

FIG. 2 is a side elevation view, in partial cross-section, of the inoculation loop device of FIG. 1.

FIG. 3 is an enlarged top plan view, in partial cross-section, of an alternative embodiment of the inoculation device having an needle-shaped inoculating end.

FIG. 4 is a side elevation view, in cross-section, of a handling tool designed in accordance with the present invention.

FIG. 5 is an enlarged, fragmentary, side elevation view, in partial cross-section, showing the releasible the engagement between the handling tool and the inoculation device.

FIGS. 6A-6C are a series of fragmentary, side elevation views, in partial cross-section, illustrating the removal of the inoculation device from a sterile container as constructed in accordance with the present invention.

FIG. 7 is a reduced, top plan view of the inoculation container as designed in accordance with the present invention.

FIG. 8 is a reduced, side elevation view, partially broken away, of the inoculation container rack of FIG. 7.

FIG. 9 is a fragmentary, side elevation view, in cross-section, of two inoculation containers mounted in back-to-back nested relation.

THE BEST MODE FOR CARRYING OUT THE INVENTION

The inoculation device of the present invention permits sterile storage and removal from the container so that the inoculating end is not tainted with undesirable foreign contaminants. Moreover, the inoculating device of the present invention facilitates greater quantitative accuracy in the volume of the inoculant dispensed. While the present invention has been described with reference to a few specific embodiments, the description is illustrative of the invention and is not to be construed as limiting the invention. Various modifications to the present invention can be made to the preferred embodiments by those skilled in the art without departing from the true spirit and scope of the invention as defined by the appended claims.

It will be noted here that for a better understanding, like components are designated by like reference numerals throughout the various figures. Attention is now directed to FIG. 1, where an inoculating device, generally designated 20, is illustrated. Inoculating device 20 includes or is formed as an elongated member 22 having an inoculation end 26 disposed on one distal end thereof, and a gripping end 24 disposed on the opposing distal end. Preferably, inoculating device 20 is composed of a moldable material, such as a styrene-based plastic. It is conceivable, however, that the inoculation device of the present invention may be metallic or formed by other techniques or with other materials.

In the preferred embodiment, inoculating end 26 is in the form of an inoculation loop end 28, as represented in FIGS. 1 and 2. Loop 28 is capable of dispensing a predetermined inoculant volume which, depending on the size of loop 28, typically incrementally varies between 1-10 microliters. Loop 28 includes an aperture 30 extending therethrough which retains the inoculant when immersed therein. Inoculation loops of this shape are generally known in the art. However, it has been discovered that variance in the cross-sectional shapes, as shown in FIG. 2, can lead to improved fluid retention and dispension accuracy. By increasing the aspect ratio (i.e., width to height ratios) of the cross-section of loop end 28 for the larger dispensing volume loop ends 28 (i.e., 10 microliters), the meniscus (not shown) formed by the inoculant fluid in the center of loop end 28 tends to be more uniform in width. Accordingly, the dispension of the inoculant can be more accurately predicted and reproduced. For a loop end 28 holding approximately 1 microliter of inoculant, the aspect ratio is preferably 1:1, while for a 10 microliter loop end 28, the aspect ration is preferably increases to 6:1.

Moreover, the casting technique developed to mold loop 28 permits substantially greater accuracy and reproducibility in controlling or setting the liquid volume carried by the loop than has been achieved for prior art inoculation loops. For example, the molds are precision crafted and aligned so that the parting lines (i.e., the lines created along the cast as a result of the separating surfaces between the two molds) are substantially minimized at loop end 28. This is particularly important where elongated body 22 intersects and is coupled to loop end 28. A parting line at this juncture tends to create a web structure therebetween which can result in fluid retention and dispension inaccuracies during operation. Such webs hold excess fluid and hamper accurate reproducibility. It has also been found that it is advantageous to keep the height of elongated member 22 substantially similar to the height of loop end 28 at this juncture. Furthermore, as will be described in much greater detail below, the method employed of calibrating the dispension volume of inoculant substantially increases the overall dispension accuracy and reproducibility.

Gripping end 24 preferably is formed as a substantially cylindrical socket or tubular structure 32 which preferably, but not necessarily, includes a slight taper inward in the mid-section thereof. In the preferred form, the longitudinal axis of socket 32 is coincident with the longitudinal axis of elongated member 22. Positioned between gripping end 24 and the opposing distal end of elongated member 22 is an annular or circular flange 38 extending radially outward from the longitudinal axis of elongated member 22. Circular flange 38 includes transverse backwall 40 which defines one end of socket 32, as illustrated in FIG. 1. Backwall 40 is substantially planar and positioned substantially perpendicular to the longitudinal axis of elongated member 22. An annular edge portion 42 of socket 32 defines a port or opening 44 allowing access to socket 32. Port 44 permits communication with the socket so that gripping end 24 of inoculation device 20 may be gripped.

As shown in FIG. 1, socket 32 can be divided into three separate, but integrally adjacent, regions. Proximate port 44 is a front section 46 defined by front wall portion 48. Preferably, although not necessarily, front section 46 is substantially cylindrical in shape. A relatively rigid annular rib 50 protrudes outward from an inner surface of front wall portion 48 into front cylindrical section 46. As best shown in FIGS. 1 and 3, a frustroconical-shaped section 52 defines the intermediate section of socket 32 and is positioned adjacent and integral with front section 46. Frustroconical section 52 is defined by intermediate wall portion 54 which is inclined inward in a direction toward backwall 40. Lastly, a back cylindrical section 56 extends from frustroconical section 52 to backwall 40 and is defined by back wall portion 58. Similar to front section 46, although smaller in diameter, back section 56 is substantially cylindrical. Accordingly, front section 46, frustroconical section 52 and back section are integrally formed and together compose socket 32.

In an alternative embodiment to the inoculation end 26 of inoculation device 20, end 26 may be formed as a needle-shaped end 29, as shown in FIG. 3. Needle-shaped end 29 is broadly known in the art, but inoculation devices having needle-shaped ends also may be used in conjunction with the present invention.

In one aspect of the present invention, a releasible handling tool or handling device, generally designated 60 and shown in FIG. 4, is provided which permits the research technician to easily grip and manually control inoculation device 20 without contaminating inoculating end 26. Handling tool 60 is formed for releasable securement to inoculation device 20 by coupling to gripping end 24 of inoculation device 20.

Handling tool 60 preferably includes an elongated body 62 similar in dimension to a ball-point pen. On one end of elongated body 62 is an inoculation device gripping end 64 which is dimensioned to be telescopically interengaged with socket 32, as shown in FIG. 5. This interengagement provides a firm coupling of the elongated body of inoculation device 20 to handling tool 60. Accordingly, elongated body 22 of inoculation device 20 can be formed to be proportionately shorter than otherwise would be the case since handling tool 60 will extend the operating length of the assembly. In the preferred embodiment, elongated inoculation device 20 can be approximately 3.5 inches in length. This relatively short length will facilitate efficient packaging of inoculation devices 20, as will be described below.

End 64 of handling tool 60 includes a cylindrical engaging portion 66 dimensioned to snugly and slidably engage the front wall portion 48 of socket 32. Furthermore, integrally formed with and protruding from the end of cylindrical engaging portion 66 is a frustroconical engaging portion 68 dimensioned to snugly and slidably engage the intermediate inner wall portion 54. As shown in FIG. 5, the degree of inward inclination of frustroconical engaging end 64 is substantially similar to the degree of inward inclination of frustroconical section 52 of socket 32. Accordingly, upon telescopic engagement between tool end 64 and gripping end 24 in the direction of arrow 74, frustroconical engaging portion 68 slidably inserts into socket 32 until the circumferential outer wall of frustroconical engaging portion 68 frictionally wedges against frustroconical inner wall portion 54 of socket 32. Similarly, the circumferential outer wall of cylindrical engaging portion 66 slidably mates with front wall portion 48 of the socket. The insertion of tool end 64 into socket 32 is limited by the wedging contact between frustroconical engaging portion 68 and frustroconical inner wall portion 54, and by the abutment of annular edge 42 against a shoulder 70 on tool 60, as best viewed in FIG. 5.

FIG. 4 illustrates that an annular retaining rib 72 extends radially outward from cylindrical engaging portion 66 proximate the intersection with frustroconical engaging portion 68. Retaining rib 72 is formed to frictionally cooperate with annular socket rib 50 protruding inwardly from front socket wall portion 48. Thus, as tool rib 72 is urged past socket rib 50, tool frustroconical surface 68 is held by the interengagement of the ribs against frustroconical socket surface 54 to produce a tight and stable coupling between the inoculation device and handling tool so that the assembly can be manipulated easily by the user as a unitary device. Upon telescopic interengagement, retaining rib 72 is frictionally and forcibly urged past annular rib 50 until retaining rib 72. This relatively simple "snap-fit" complementary arrangement provides a stable, releasably coupling of inoculation device 20 to handling tool 60. Such a simple arrangement between these two unitary "snap-fit" parts (i.e., tool end 64 and gripping end 24) minimize coupling efforts and eliminate moving parts. More importantly, this arrangement facilitates coupling by a simple insertion of the tool into the inoculation device and thereby reduces the potential for contamination of the inoculating end 26 which could occur through unintentional contact during more complex manipulation of components.

It will be appreciated that the front wall socket portion 48 could define an annular recess portion (not shown) extending radially outward from socket 32. The annular recess portion would be formed to matingly cooperate with annular retaining rib 72 of tool end 64. Similarly, the cylindrical engaging portion 68 of tool end 64 could define an annular recess (not shown) extending radially inward therefrom. This cylindrical engaging portion annular recess would be formed to matingly cooperate with annular socket rib 50 of socket 32.

As noted, to couple tool end 64 with socket 32, tool end 64 is preferably urged along the longitudinal axis of elongated member 22, which is in the axial direction of arrow 74. Accordingly, the longitudinal axis of elongated body 62 is preferably coincident with the longitudinal axis of elongated member 22. Although not necessary to practice the present invention, such an orientation is desirable for the ease of coupling and for manipulation purposes.

It is apparent that tool 64 includes a male end portion while gripping end 24 includes a complementary female engageable portion. It will be appreciated, however, that gripping end 24 may be formed as the male engageable portion, while handling tool 60 includes the complementary female portion without departing from the true spirit and nature of the present invention. To release inoculation device 20 from handling tool 60, the interengagement between retaining rib 72 and annular rib 50 must be overcome. Therefore, means for providing a separating force pushing or pulling inoculation device 20 and handling tool 60 in opposite axial directions is desirable. In the preferred embodiment, an extendable tip 76 projects from tool end 64 and which is formed to engage socket backwall 40, as shown in FIG. 5. Tip 76 is positioned in a normally retracted orientation (FIG. 4) and reciprocally mounted inside cylindrical engaging portion 68 so as to be extendable in the axial direction of arrow 74 (FIG. 5). Accordingly, to release inoculation device 20 from handling tool 60, tip 76 is urged forward until it contacts backwall 40. Tip 76 presses against backwall 40 until the reaction or separating force overcomes the frictional engagement between retaining rib 72 and annular rib 50, at which point inoculation device 20 releases from handling tool 60.

Referring back to FIG. 4, tip 76 is coupled to a shaft 78 centrally positioned longitudinally through elongated body 62 of handling tool 60. Again, reminiscent of a ball-point pen, shaft 78 is slidably reciprocatable through elongated body 62 so that tip 76 may be extendable from the distal end of engaging end 64. A compression spring member 80 (schematically shown) resiliently biases shaft 78 toward the retracted position.

In the preferred form, a manually engageable button 82 is coupled to shaft 78 so that button 82 can drive tip 76. Accordingly, when button 82 is pressed in the direction of arrow 74, tip 76 is proportionately urged forward to an extended position. Upon disengagement of button 82, spring member 80 urges shaft 78 and tip 76 back to its normally retracted position. Turning now to FIG. 7, another aspect of the present invention will be described. Briefly, in accordance with the present invention, a plurality of inoculation devices 20 are stored in a container, generally designated 84, which includes a plurality of storage cavities 86 for individual storage of each inoculation device 20. As best viewed in FIGS. 7 and 8, individual cavities 86 are aligned in a row and column matrix for efficient grouping. For the ease of description, however, only a single container cavity 86 will be described henceforth.

As shown in FIGS. 6A-6C, cavities 86 are basically elongated, test tube-shaped cavities. Cavity 86 is preferably cylindrical and is dimensioned to receive and store inoculation device 20 in an orientation such that opening or port 44 of socket 32 is positioned proximate a storage cavity opening 88. FIGS. 6A-6C and 7 illustrate that opening 88 is defined by an upwardly facing container surface 90. Accordingly, to store inoculation device 20 in this orientation, an upper cavity portion 92 of storage cavity 86 is dimensioned to receive both gripping end 24 and circular flange 38 of inoculation device 20. A lower cavity portion 94 of storage cavity 86 is dimensioned to receive elongated body 22 and the inoculating end. Thus, if the inoculating end comprises inoculating loop 28, as opposed to needle-shaped end 29 (FIG. 3), lower cavity portion 94 must be dimensioned to slidably or freely receive loop end 28 without damaging it upon removal. Regardless, lower cavity portion 94 may be smaller in cross-section than that of upper cavity portion 92.

Both upper cavity portion 92 and lower cavity portion 94 are aligned along the same longitudinal axis and intersect at an upwardly facing annular shoulder 96 extending around the inner cavity perimeter, as best shown in FIG. 6C. Shoulder 96 is formed to allow circular flange 38 to seat thereagainst, thereby preventing circular flange 38 from entering lower cavity 94. Such seating performs two main functions: first, it prevents loop end 28 from axially engaging the inner walls of lower cavity portion 94, which prevents damage to loop end 28; second, shoulder 96 provides support for gripping end 24 when tool end 64 is urged into socket 32.

A sheet-like cover or wall, generally designated 98, is positioned across cavity opening 88 and sealed hermetically to container surface 90. Container 84 with inoculation devices 20 sealed in cavities 86 may be sterilized at the packaging facility, for example, by auto-claving, or by irradiation with radioisotopes or an electron beam. The inner walls of upper and lower cavity portions 92 and 94, inner surface 102 of cover sheet 98, and inoculation device 20 all will be sterilized at packaging.

Cover sheet 98 preferably is a thin, relatively frangible material which is capable of being punctured, as will be described below. Moreover, cover 98 should be non-porous so as to provide a barrier maintaining the interior of the container in a sterile condition. Thus, outer cover surface 104 may be non-sterile and may be handled without affecting the sterility of inoculation device 20. Preferably, cover 98 is a thin metallic foil, such as aluminum, but may comprise other materials as well.

An adhesive is to be applied to either container surface 90 or inner surface 100 of cover sheet 98, except for inner central surface 102, so that sheet-like cover 98 may be securely attached to container surface 90 to provide hermetic and sterile sealing of cavity 86. During placement of cover 98 over cavity opening 88, cover 98 is stretched relatively taunt to facilitate puncturing and deformation of cover 98.

In accordance with the container/inoculation device arrangement of the present invention, inoculation device 20 can be removed from storage cavity 86 while retaining the full sterility of inoculating end 26. As mentioned, inoculation device 20, storage cavity 86 and the inner central surface 102 of first surface 100 are all sterile so that inoculation end 26 will not become contaminated by contact with those non-sterile portions of container 84. Accordingly, when removed from cavity 86, inoculation device 20 is maintained out of contact with unsterile portions of container rack 84.

As specifically designed, handling tool 60 is formed to securely couple to inoculation device 20, and is, thus, most appropriate to remove inoculation device 20 from sealed storage cavity 86. Because of the hermetic sealing provided by cover 98 over cavity opening 88, frangible cover 98 must be punctured so that inoculation device 20 can be accessed. As shown in FIG. 6A, tip 76 of handling tool 60 punctures cover 98 by creating a pin-like access opening therethrough. Since cover 98 is thin, relatively taunt, frangible or deformable material, piercing or puncturing of cover 98 by tip 76 is easily accomplished.

As handling tool 60 is driven downward in the direction of arrow 106, the access opening is continually widened in diameter as tip 76, because of its angular inclination outward, protrudes into cavity 86. Expansion of the aperture continues as frustroconical engaging portion 68 of engaging end 64 passes through cavity opening 88. FIG. 6A and 6B illustrate that deformable punctured portions 108 which define the access opening through cover 98 are directed inwardly into cavity 86 by handling tool 60 as it passes through and widens the access aperture. Thus, the sterile inner central surface 102 of deformable punctured portions 108 only contact the side walls of upper cavity portion 92, which are also sterile. Accordingly, the inner central surface 102 of deformable punctured portions 108 remain substantially sterile despite being bent inward.

Subsequently, as shown in FIG. 6B, engaging end 64 of handling tool 60 is inserted into socket 32 so that inoculation device 20 can be releasably coupled to handling tool 60, as described above. Circular flange 38 is supported against annular shoulder 96 permitting proper coupling of the tool and inoculation device 20.

As inoculation device 20 is withdrawn from cavity 86 in the direction of arrow 110, as shown in FIG. 6C, circular flange 38 nears opening 88, and an upwardly facing rim portion 112 of circular flange 38 engages inwardly directed deformable punctured portions 108 (FIGS. 6A and 6B) of cover 98 and redirects them outwardly in a direction away from cavity 86 (FIG. 6C). By repositioning punctured portions 108 outward and away from cavity 86, the sterile inner central surface 102 of punctured portions 108 will be facing radially inward toward inoculation device 20. Therefore, should there be any contact of inoculating end 26 with deformable puncture portions 108 of cover 98, such contact will be with the sterile inner central surface 102. This permits removal of inoculation device 20 while preserving its sterility. Accordingly, inoculation device 20 may be completely removed from cavity 86 in a sterile condition and will be ready for use.

By contrast, the metallic inoculation loops of the prior art devices required a time consuming sterilization process before each use. Prior art plastic inoculation devices, on the other hand, have been individually or multiply packaged in sealed plastic bags. Hence, when a variety of media requires inoculation, access to the inoculation devices becomes burdensome and tedious. In the present invention, an inoculation kit assembly is provided which permits quick and easy access to the individual inoculation devices while preserving sterility of each of the inoculating ends. Tip 76 of handling tool 60 easily punctures cover 98 which seals opening 88 so that tool end 64 quickly and accurately grips or couples to gripping end 24. Handling tool 60 is then withdrawn, which efficiently removes inoculation device 20 from cavity 86 while maintaining inoculation device 20 out of contact with unsterile portions of container 84. The used inoculation device then can be easily ejected from the tool by pressing button 82, and the procedure can be repeated quickly and efficiently, while always preserving sterility of inoculating end 26.

A removable dust cover (not shown) may be provided over cover 98 to protect outer cover surface 104 and reduce the accumulation of unsterile particles and dust thereon. This dust cover may be deployed or removed at the user's convenience, but is particularly suitable when the container/inoculation device arrangement is not in use or is placed in storage. Additionally, after the dust cover has been removed, a swab doused in a sterilizing substance, such as alcohol, may be used to wipe a portion or all of outer cover surface 104. This technique will further enhance sterility in the event a sterile inoculation device 20 inadvertently contacts outer cover surface 104.

It is, of course, preferable to group a plurality of inoculation devices 20 into a single container 84 as opposed to individual containers. Referring back to FIGS. 7 and 8, it may be seen that container rack 84 preferably includes a plurality of storage cavities 86 which are disposed and aligned in a side-by-side relation. Moreover, to further promote efficient grouping, cavities 86 are aligned in a array of rows and columns, as shown in FIG. 7, where the adjacent rows and adjacent columns are in a staggered relationship.

FIG. 8 illustrates that multiple cavity container or container rack 84 includes side walls 114 extending downward from the perimeter of container surface 90. Container rack 84 is a fairly rigid material, and is preferably a polypropylene-based plastic. It will be noted, however, that container rack 84 may be composed of a metallic material or the like without departing from the true spirit and nature of the present invention. Furthermore, it will be appreciated that container rack 84 is of sufficient weight to maintain stability against a working surface during use without requiring manual engagement thereof by the user. Only one hand need be applied by the technician to pierce cover 98 with handling tool 60, insert engaging end 64 into socket 32, and withdraw inoculation device from cavity 86. Hence, because of the weight of container rack 84, contact of circular flange 38 with punctured portions 108 upon withdraw will not cause container rack 84 to tip over or lift up off the working surface. This is true even if only one inoculating device 20 remains stored in storage cavities 86.

In an alternative embodiment, a second container rack 84' may be mounted in back-to-back nested relation to first container rack 84. As best viewed in FIGS. 6A-6C, 8 and 9, first and second container racks 84 and 84' include backsides 116 and 116' which oppositely faces container surfaces 90 and 90'. Backsides 116 and 116' include cavity outer walls 118 and 118' which define cavities 86 and 86'. As best shown in FIG. 9, adjacent cavity outer walls 118 and 118' define slots 120 and 120' which are dimensioned to receive the corresponding cavity outer walls 118 and 118' of mating container racks. In other words, slots 120 formed between adjacent outer walls 118 of first container rack 84 nest with corresponding outer walls 118' of second container rack 84'. Moreover, slots 120' formed between adjacent outer walls 118' of second container rack 84', nest with corresponding outer walls 118 of first container rack 84. Accordingly, when first container rack 84 is moved in the direction of arrow 122, upon slidable interengagement between the corresponding and oppositely opposing backsides 116 and 116' first container rack 84 will interlock or snap together with second container rack 84'.

This alternative configuration is twice as efficient as a single container rack 84. Not only is the packing density increased two-fold, the operable access to each inoculation device 20 remains the unchanged. For example, after the research technician has completely exhausted use of first container rack 84, they may simply flip the container rack 84 over so that second container rack 84' may be accessed.

It will be noted that preferably, first and second container rack 84 and 84' are virtually identical in dimension. The staggered rows and columns of cavity outer walls 118 and 118' which define corresponding backsides 116 and 116' will be properly align so that two identical container racks 84 and 84' can be nested together in the fashion just described. As shown in FIGS. 6A-6C, side walls 114 and 114' are dimensioned to abut one another and enclose the cavity outer walls 118 and 118' defining cavities 86 and 86'. Nested container racks 84 and 84' efficiently use space and permit easy accessibility to inoculation devices 20 from either side.

Moreover, in the preferred form, a locking mechanism is provided which removably locks container racks 84 and 84' together. As best viewed in FIGS. 7 and 8, one side wall 114 includes a least one locking tab 113 extending downwardly from the inward facing surface of the one side wall 114, while the opposite end side wall 114 provides a mating slot 115 extending therethrough. When container racks 84 and 84' are turned back-to-back for nesting, a similarly formed locking tab (not shown) of second container rack 84' engages aligned mating slot 115 of first container rack 84. Similarly, locking tab 113 of first container rack 84 engages a similarly formed aligned mating slot (not shown) of second container rack 84'. Thus, this configuration cooperates to removably lock first and second container racks 84 and 84' in the back-to-back nested relation.

In addition, a plurality of alignment posts 117, as shown in FIGS. 6A-6C, 8 and 9, may be provided which facilitate alignment of abutting side walls 114 and 114' when container racks 114 and 114' are nested together. Posts 117 and 117' are offset from each other and extend downwardly from the inward facing surfaces of side walls 114 and 114', similar to locking tabs 113.

The present invention provides a method for removing sterile inoculation device 20 from sterile storage container 84 while maintaining inoculation end 26 of inoculation device 20 in a sterile condition. The method comprises the steps of puncturing a wall or cover 98 of storage container 84 proximate gripping end 24 of inoculation device 20 with handling tool 60 to form an access opening to container 84. Inoculation device 20 is coupled to handling tool 60 through the access opening by urging handling tool 60 toward inoculation device 20 until it releasably couples to handling tool 60. Subsequently, inoculation device 20 and handling tool 60 are withdrawn out of container 84 through the access opening without contacting inoculation end 26 with unsterile portions of container 84.

As cover 98 is punctured, punctured portions 108 are directed inwardly toward container 84 through contact with handling tool 60. The present invention further includes the step of redirecting inwardly directed punctured portions 108 of cover 98 outwardly and away from container 84 by annular flange 38 during the withdrawing step.

The method includes releasing inoculation device 20 from handling tool 60 by pressing against backwall 40 of inoculation device 20 with tip 76 extendably mounted to handling tool 60. Tip 76 is extendable in the direction of arrow 74 (FIG. 5) which is away from inoculation device 20 until device 20 is released from handling tool 60.

In another aspect of the present invention, the accuracy of the dispensing volume of inoculating loop 28 is substantially increased by employing a radioisotope method of calibration to calibrate the casting mold which defines inoculation device 20. Using this method to calibrate the mold, a greater dispension accuracy can be attained because the mold may be more fined tuned to reproduce a greater precision inoculating loop 28. This technique has reduced the dispensing volume variation to as little as ±3% which is far more accurate than the 60% variation of the prior art devices.

As previously mentioned, the prior art method relied on the "Evan's Blue Dye" method for calibrating the dispensing volume of the inoculating loop. Because the "Evan's" method of calibration appears to be less reliable, the actual accuracy of the volume dispensed can only be as accurate as the calibration method, at best. That is, even if the dispensing volume were substantially accurate, the "Evan's" method of volume calibration could not be relied upon to yield an accurate measurement as compared to the radioisotope method of calibration of the present invention which is to be described henceforth.

In accordance with the present invention, the casting molds of the inoculation devices were calibrated using a radioisotope method of calibration. This method is calibration is far more accurate than the methods employed in the prior art devices. Accordingly, the present invention provides a method for calibrating an inoculation device casting mold which increases the dispension accuracy of inoculation end 26. The method of calibration comprises the steps of forming an inoculation device from a moldable material using a casting mold. Subsequently, the inoculation end 26 is immersed in a first aqueous fluid, preferably distilled water, having a known concentration of a radioisotope compound (i.e., radioisotopes per cubic centimeter). The next step requires dispensing the first fluid carried by the immersed inoculation end 26 into a second fluid, or by rinsing the immersed inoculation end 26 with a predetermined amount of the second fluid, preferably 100 microliters. The second fluid, also, preferably is distilled water and has a known concentration of the radioisotope which is usually zero. Usually, dispensing is accomplished by immersing the inoculation end 26 in the second fluid and moving the end about to disperse the radioisotopes therein. Subsequently, the number of radioisotopes in the second fluid is measured or counted using a counter such as a BECKMAN TM LS 3801 liquid scintillation counter. By knowing the radioisotope concentration of the first fluid and knowing the concentration of radioisotopes measured in the second fluid, the liquid volume carried by inoculation end 26 can be determined or calculated to thereby calibrate the mold. Additionally, the casting mold may have its volume adjusted and the procedure repeated until the desired volume is attained. This method can be used for loop-type and needle-type inoculation ends.

What is claimed is:

1. An inoculation kit assembly comprising:
    an inoculation device including an elongated member having an inoculation end and an opposed gripping end;
    container means including a cavity with an opening into said cavity, said cavity being dimensioned to receive said inoculation device, said inoculation device being positioned in said cavity for grasping of said gripping end through said opening;
    sheet cover means positioned across and sealing said opening and retaining said inoculation device in said cavity, said cover means having an inner central surface facing said cavity and an opposite facing unsterile outer surface; and
    handling tool means capable of telescopic engagement with said gripping end of said inoculation device through said opening for releasable grasping of said gripping end;
    said cavity, said inoculation device and said inner surface facing said cavity all being sterile, said cover means being formed of a deformable material capable of being punctured by said handling tool from said outer surface and said cover means being spaced from said inoculation device such that said material is displaced by said handling tool into said cavity during grasping of said gripping end to a position in said cavity for unimpeded grasping of said gripping end and said material is displaced outwardly away from said cavity during removal of said inoculation device through said opening while maintaining said inoculation device out of contact with unsterile portions of said container means and said cover means.

2. The inoculation kit assembly as defined in claim 1 further including:
    retaining means provided on at least one of said gripping end and said handling tool means for releasably sustaining relative telescopic engagement between said gripping end and said handling tool means.

3. The inoculation kit assembly as defined in claim 1 wherein,
    said retaining means is formed for frictional engagement between said gripping end and said handling tool means.

4. The inoculation kit assembly as defined in claim 3 wherein,
    said handling means includes a protruding end, and
    said gripping end includes a socket dimensioned to slidable receive said protruding end for frictional engagement therebetween.

5. The inoculation kit assembly as defined in claim 4 wherein,
    said retaining means is provided by an annular rib portion in a wall defining said socket, said rib portion protruding radially inwardly into said socket; and an annular recess formed in said protruding end and matingly receiving said rib portion.

6. The inoculation kit assembly as defined in claim 4 wherein,
    said handling tool means includes a tip member reciprocally mounted with respect to said protruding end and capable of puncturing said material.

7. The inoculation kit assembly as defined in claim 1 wherein,
    said cover means is formed of a metallic foil which is deformable inwardly toward said cavity during puncture of said cover means and is deformable outwardly away from said cavity during removal of said inoculation device.

8. The inoculation kit assembly as defined in claim 7 wherein, said inoculation device includes redirecting means formed to redirect the punctured material away from said inoculating end during said removal from said cavity.

9. The inoculation kit assembly as defined in claim 1 wherein,
said container means is formed to define a plurality of separate, similarly formed cavities having openings thereto and comprising a set of cavities,
a plurality of individual inoculation devices each having an inoculation end and an opposed gripping end with one inoculation device mounted in each cavity of said set of cavities,
said sheet cover means being positioned across and sealing each opening in said first set of cavities to retain said inoculation devices therein, and
each cavity, inoculation device and the surface of said cover means facing said cavity being sterile.

10. The inoculation assembly as defined in claim 8 wherein,
said redirecting means comprises an annular flange extending radially from sides of said inoculation device.

11. The inoculation assembly as defined in claim 10 wherein,
said annular flange is positioned proximate said gripping end.

12. The inoculation assembly as defined in claim 1 wherein,
said container means defining said cavity includes an upwardly facing annular shoulder extending around the inner perimeter of said cavity and positioned relative said inoculation device such that a portion of said gripping end supportably seats against said shoulder.

13. The inoculation assembly as defined in claim 1 wherein,
said inoculation end of said inoculation device comprises a loop capable of retaining an inoculant.

14. The inoculation assembly as defined in claim 13 wherein,
said loop is precalibrated in size such that said retained inoculant is substantially of a predetermined volume.

15. The inoculation assembly as defined in claim 1 wherein,
said inoculation end of said inoculation device is a needle-shaped end.

16. The inoculation assembly as defined in claim 1 wherein,
said cover means is formed of a metallic foil.

17. The inoculation assembly as defined in claim 9 wherein,
each said cavity of said first set of cavities is disposed in a side-by-side relation and positioned in a substantially similar orientation.

18. The inoculation assembly as defined in claim 17 wherein,
said cavities in said first set of cavities are aligned in an array of rows and columns.

19. The inoculation assembly as defined in claim 18 wherein,
adjacent rows of said cavities are in a staggered relation to one another.

20. The inoculation assembly as defined in claim 19 wherein,
said container means defining said first set of cavities includes in each cavity an annular shoulder positioned relative said individual inoculation devices to support the inoculation device in said cavity by the respective gripping end.

21. The inoculation assembly as defined in claim 20 wherein,
said container means is formed to define a second set of cavities including a plurality of cavities formed with openings thereto and dimensioned substantially similar to said first set of cavities, said first set of cavities and said second set of cavities being oriented in said container means in back-to-back opposed nested relation with the openings of the first set of cavities and the openings of the second set of cavities facing outwardly on opposite sides of said container means.

22. The inoculation assembly as defined in claim 21 wherein,
said container means is provided by a first container member formed of a moldable material and having said first set of cavities molded therein, and a second container member formed of a moldable material and having said second set of cavities molded therein; and
said first container member and said second container member further being secured together in nested back-to-back relation.

23. The inoculation assembly as defined in claim 22, further including:
locking means coupled between said first container member and said second container member for removably locking said first and said second container members together in said nested back-to-back relation.

24. The inoculation assembly as defined in claim 23, wherein,
said locking means includes at least one locking tab extending outwardly from one of said first container member and said second container member, and one of said first container member and said second container member includes at least one aligned mating slot formed and dimensioned to receive said locking tab for locking engagement therebetween when said first and said second container members are nested in said back-to-back relation.

25. The inoculation assembly as defined in claim 21 and,
an inoculation device mounted in each cavity of said second set of cavities,
cover means extending across and sealing each opening in said second set of cavities to retain the inoculation device therein, and
said cavities in said second set of cavities, the inoculation devices in said second set of cavities and the inside surface of the cover means covering said second set of cavities all being sterile.

26. The inoculation assembly in claim 25 wherein,
said cover means covering the openings to said first set of cavities and the cover means covering the openings to the second set of cavities are each provided by a sheet of metallic foil adhesively secured to said container means proximate the openings to said first set of cavities and proximate the openings to said second set of cavities.

27. An inoculation assembly comprising:
an inoculation device including an elongated member having an inoculation end and an opposed gripping end having a perimeter wall and a transversely extending backwall defining a socket;

handling tool means including a protruding end formed and dimensioned for sliding receipt in said socket for relative telescopic engagement along a longitudinal axis of said elongated member with said gripping end of said inoculation device;

retaining means for releasably sustaining relative telescopic frictional engagement between said protruding end and said socket including an annular rib portion protruding radially inward from said perimeter wall into said socket, and a radially protruding rib extending from said protruding end formed to matingly cooperate with said annular rib portion to cause said frictional engagement; and said handling tool means includes an extendable tip movably mounted to said protruding end, said tip being mounted for movement relative to said protruding end between a normally retracted position and an extended position, said tip in said extended position engaging said backwall and producing sufficient displacement of said socket relative to said protruding end to release said socket of said inoculation device from frictional engagement with said protruding end of handling tool means.

28. The inoculation assembly as defined in claim 27 wherein,
said handling tool means includes an elongated body having a manually grippable end opposite said protruding end.

29. The inoculation assembly as defined in claim 27 wherein,
said extendable tip is operably coupled to button means positioned on the opposing distal end of the elongated body of said handling means.

30. The inoculation assembly as defined in claim 27 wherein,
said wall defining said socket is substantially cylindrical.

31. The inoculation assembly as defined in claim 30 wherein,
a portion of said wall is inclined radially inward, and said protruding end includes a mating wall dimensioned to snugly engage said portion of said wall during said telescopic engagement.

32. The inoculation assembly as defined in claim 27 wherein,
said inoculation end of said inoculation device comprises a loop capable of retaining an inoculant.

33. The inoculation assembly as defined in claim 32 wherein,
said loop is precalibrated in size such that said retained inoculant is substantially of a predetermined volume.

34. The inoculation assembly as defined in claim 27 wherein,
said inoculation end of said inoculation device is a needle-shaped end.

35. The inoculation assembly as defined in claim 27 wherein,
said protruding end is sufficiently pointed to enable puncturing of a sheet of metallic foil mounted across an opening to a container.

36. The inoculation assembly as defined in claim 27 wherein,
said extendable tip is sufficiently pointed to puncture a metallic foil mounted across an opening to a container.

37. A method of removing a sterile inoculation device from a sterile storage container while maintaining an inoculation end of said inoculation device in a sterile condition, comprising the steps of:
puncturing a wall of said storage container proximate a gripping end of said inoculation device with a handling tool by displacing portions of said wall inwardly toward said container through contact with said handling tool to form an access opening to said container;

coupling said inoculation device to said handling tool through said access opening by urging said handling tool toward said inoculation device until said inoculation device is releasably coupled to said handling tool; and withdrawing said handling tool and said inoculation device out of said container through said access opening without contacting said inoculation end with unsterile portions of said container by redirecting the inwardly displaced portions of said wall outwardly and away from said container.

38. The method of removing a sterile inoculation device as defined in claim 37 wherein,
said redirecting step is accomplished by contacting said inwardly displaced portions of said wall with redirecting means carried by one of said gripping end of said inoculation device and said handling tool.

39. The method of removing a sterile inoculation device as defined in claim 37, and the step of:
releasing said inoculation device from said handling tool by displacing said inoculation device with an extendable member carried by said handling tool until said inoculation device is released from said handling tool.

40. A sterile inoculation assembly comprising:
a plurality of individual elongated inoculation devices each having an inoculation end and an opposed gripping end;

a first container member defining a first set of separate side-by-side cavities aligned in an array of similarly spaced rows and columns in staggered relation to one another, each said cavity including an opening therein and dimensioned to receive one inoculation device of said plurality of devices in a manner disposing said gripping end for grasping through said opening, and each said cavity having an annular shoulder positioned relative respective individual inoculation devices to support the inoculation device in said cavity by the respective gripping end;

a second container member defining a second set of separate side-by-side cavities aligned in an array of similarly spaced rows and columns in staggered relation to one another, each said cavity dimensioned substantially similar to said first set of cavities, and said first container member and said second container member being oriented in back-to-back opposed nested relation with the openings of the first set of cavities and the openings of the second set of cavities facing outwardly on opposites sides thereof;

sheet cover means positioned across and sealing each said opening in said first set of cavities and said second set of cavities to retain said respective inoculation devices in said cavities; and locking means coupled between said first container member and said second container member for removably locking said first and said second container members in said nested back-to-back relation;

said cavities, said inoculation devices and an inner central surface of said cover means each being sterile, and said cover means being formed of a material capable of being punctured for grasping of respective gripping ends and removal of said inoculation device through said opening while maintaining said inoculation device out of contact with unsterile portions of said container means and said cover means.

41. The inoculation assembly as defined in claim 40, wherein, said locking means includes at least one locking tab extending outwardly from one of said first container member and said second container member, and one of said first container member and said second container member includes at least one aligned mating slot formed and dimensioned to receive said locking tab for locking engagement therebetween when said first and said second container members are nested in said back-to-back relation.

42. An inoculation assembly comprising:

an inoculation device including an elongated member having an inoculation end and an opposed gripping end having a socket;

handling tool means including a protruding end formed for sliding receipt in said socket for telescopic engagement with said gripping end of said inoculation device along a longitudinal axis of said elongated member, said protruding end being sufficiently pointed to enable puncturing of a sheet of metallic foil mounted across an opening to a container; and retaining means provided on at least one of said gripping end and said handling tool means for releasably sustaining relative telescopic frictional engagement between said gripping end and said handling tool means.

43. An inoculation kit assembly comprising:

an inoculation device including an elongated member having an inoculation end and an opposed gripping end defining a socket;

container means including a cavity with an opening into said cavity, said cavity being dimensioned to receive said inoculation device, said inoculation device being positioned in said cavity for grasping of said gripping end through said opening;

sheet cover means positioned across and sealing said opening and retaining said inoculation device in said cavity, said cavity, said inoculation device and an inner surface of said cover means facing said cavity all being sterile, and said cover means being formed of a material capable of being punctured for grasping of said gripping end and removal of said inoculation device through said opening while maintaining said inoculation device out of contact with unsterile portions of said container means;

handling tool means including a protruding end formed for sliding receipt in said socket for telescopic engagement with said gripping end of said inoculation device, said protruding end including a tip member reciprocally mounted with respect to said protruding end and capable of puncturing said material; and retaining means provided on at least one of said gripping end and said handling tool means for releasably sustaining relative telescopic frictional engagement between said gripping end and said handling tool means.

* * * * *